United States Patent [19]

De Paoli Ambrosi

[11] Patent Number: 6,147,054
[45] Date of Patent: Nov. 14, 2000

[54] COMPOSITION FOR COSMETIC, PHARMACEUTICAL OR DIETETIC USE BASED ON AN AMINO SUGAR AND/OR A POLYHYDROXYLIC ACID

[76] Inventor: Gianfranco De Paoli Ambrosi, Via Cure del Lino 32, Salò (Brescia), Italy

[21] Appl. No.: 08/971,436

[22] Filed: Nov. 17, 1997

[30] Foreign Application Priority Data

Nov. 29, 1996 [IT] Italy ................................. BS96A0094

[51] Int. Cl.[7] ........................ A61K 31/70; A61K 31/525; A61K 31/51; A61K 31/44; A61K 31/355; A61K 31/34; A61K 35/78

[52] U.S. Cl. .................. 514/23; 514/24; 514/25; 514/52; 514/251; 514/276; 514/332; 514/458; 514/474; 424/195.1

[58] Field of Search .................. 514/23, 24, 25, 514/276, 332, 52, 251, 458, 474; 424/195.1

[56] References Cited

U.S. PATENT DOCUMENTS

| 5,100,879 | 3/1992 | Ueno et al. | 514/59 |
| 5,538,731 | 7/1996 | Shimomura et al. | 424/401 |

OTHER PUBLICATIONS

An Encyclopedia of Chemicals, Drugs and Biologicals, 1996, The Merck Index, Encyclopedia.
ID: 9004–61–9 (CAS RN No.), Oct. 29, 1999, Systematic Name: Hyaluronic Acid (EINECS:MESH:TS CAINV), National Library of Medicine.
ID:7512–17–6 (CAS RN No.), OCt. 29, 1999, Systematic Name: N–Acetyl–Beta–D–Glucosamine (EINECS), National Library of Medicine.
ID:6556–12–3 (CAS RN No.), ID:576–37–4 (CAS RN No.), Oct. 29, 1999, Systematic Name: Glucuronic Acid (EINECS D–Glucuronic Acid (TSCAINV), National Library of Medicine.

*Primary Examiner*—Kevin E. Weddington
*Attorney, Agent, or Firm*—McGlew & Tuttle, P. C.

[57] ABSTRACT

A composition for cosmetic, pharmaceutical or dietetic use and including as the active ingredient, at least one of the substances which include acetylglucosamine and glucuronic acid in combination with the active ingredients which belong to the chemical class of the carboxylic acids, α-hydroxy acids, vitamins, amino acids, and bioflavonoids, and formulated with particular synergists, additives, and excipients for external use or for internal use.

23 Claims, No Drawings

COMPOSITION FOR COSMETIC, PHARMACEUTICAL OR DIETETIC USE BASED ON AN AMINO SUGAR AND/OR A POLYHYDROXYLIC ACID

SUMMARY AND OBJECTS OF THE INVENTION

The object of the present invention is a novel composition for cosmetic, pharmaceutical or dietetic use that is essentially intended for external use to be applied either on intact or injured skin, or on the mucous membranes, and for internal use, taken in the form of tablets, delayed-action tablets, capsules, syrup, drops, suppositories or in any other pharmaceutical form intended for the taking of the drug orally, or injected intramuscularly, intravenously, subcutaneously, intra-articularly or in any other form intended for the administration of the composition in question by means of injection.

More specifically, the present invention pertains to a composition for the above-mentioned use, which is characterized in that it contains, as the active ingredient, at least one of the substances which include acetylglucosamine and glucuronic acid in combination with the active ingredients which belong to the chemical class of the carboxylic acids, α-hydroxy acids, vitamins, amino acids, and bioflavonoids, and formulated with particular synergists, additives, and excipients for external use or for internal use.

Acetylglucosamine and glucuronic acid may, by way of indication, also be described as precursors of the glycosaminoglycans. As used herein, the term glucuronic acid includes both glucuronic acid itself and glucuronic acid lactone as the corresponding cyclized form thereof.

The stimulation of the biosynthesis or even the simple supply of suitable biochemical precursors, which may be described, from a purely chemical point of view, as molecular elements that, alone or combined, constitute the monomers or the parts of the monomers of the various polysaccharide structures, specifically the glycosaminoglycans, which can constitute the polysaccharide fraction of the proteoglycan structures, produces beneficial biological effects on the treatment of the skin against the effects of aging and for the course of treatment of the various conditions of the skin, of the joints, and the like.

The purpose of the present invention is precisely to provide a cosmetic, pharmaceutical, or dietetic composition, which is able to develop and to sustain even such biological effects, among others, containing mainly acetylglucosamine and glucuronic acid in combination with the active ingredients belonging to the chemical class of the carboxylic acids, α-hydroxy acids, vitamins, amino acids, flavonoids, and polysaccharides.

By way of indication, the effects that may be achieved are direct and are expressed as:

biological, physiological, chemical, physical, pharmacological action by the acetylglucosamine and the glucuronic acid either alone or combined;

a biological, physiological, chemical, physical, or pharmacological action of the polysaccharide and/or proteoglycan molecular structures obtained by means of the stimulation of the endogenous biosynthesis starting from the molecular structures of the acetylglucosamine and of the glucuronic acid, either alone or combined;

or the effects are indirect and are expressed as:

biological, physiological, chemical, physical, or pharmacological action of the polysaccharide molecular structures obtained by means of the stimulation of the endogenous biosynthesis of the molecular structures of the glycosaminoglycans and of the proteoglycans, with other molecular or macromolecular structures present in the human body with which they would or may interact.

For their synthesis, some glycosaminoglycans have an active metabolite that is basically represented by UDP-N-acetylglucosamine, which has a precursor in acetylglucosamine.

Acetylglucosamine belongs to the class of amino sugars, and is widespread in nature in the form of repetitive polymers of the same molecular unit to form complex structures, such as chitin, and constitutes one of the two molecular fractions which form the monomer of the various glycosaminoglycans, including hyaluronic acid.

Glucuronic acid, joined with acetylglucosamine by a 1-4-β-glycosidic bond, forms the monomer of hyaluronic acid.

Thus, glucuronic acid acts as a precursor of hyaluronic acid either alone or combined with the acetylglucosamine.

Acetylglucosamine and glucuronic acid have the property of preventing the hyperoxidative phenomena, which, among other things, may have an effect on the macromolecules of a polysaccharide nature, e.g., the hyaluronic acid.

However, by way of indication and not exhaustively, the action exerted by the acetylglucosamine and by the glucuronic acid towards the stimulation of the biosynthesis of the glycosaminoglycans and the proteoglycans and, consequently, the multiphasic and multicentric action of the identical glycosaminoglycans and proteoglycans on the skin, on the joint zones and on the other organic regions are combined.

The therapeutic role played by acetylglucosamine, by glucuronic acid, and by their interaction thus appears to be clear in all those pathological forms, in which it becomes necessary to stimulate the endogenous production, e.g., of hyaluronic acid.

In the field of cosmetics, since a reduction in the amount of hyaluronic acid present in the skin occurs during aging, with resulting dehydration of the skin, appearance of wrinkles and loss of elasticity and of tonicity of the skin, the action exerted by acetylglucosamine, by glucuronic acid and by the related combination is of considerable importance.

In addition, the action of the glycosaminoglycans, whose production may be stimulated by the acetylglucosamine and by the glucuronic acid, either alone or combined, also involves, among other things, the other structures of the skin, such as the collagens, the elastic fibers, and the structural proteins, so that a stimulation by means of the above-mentioned biochemical precursors of the glycosaminoglycans and of the proteoglycans of the amorphous matrix of the skin leads to aesthetically and pharmacologically relevant results.

The action exerted by the acetylglucosamine and by glucuronic acid, either alone or combined, with other active ingredients of a flavonoid nature either in the pure form or contained in extracts of plants or fruits or of parts of plants also proves to be particularly important in fighting against the problems which are associated with the biological, physiological, as well as physiopathological or pathological regression of the circulation and of the microcirculation.

In fact, it appears to be justified to consider, besides parietal factors, the existence of extraparietal factors, which may interfere with many functional aspects of the wall of a vessel, both in physiological conditions and especially in pathological conditions.

In fact, it is fair to believe that not only the permeability of the small vessels, but also the parietal reactive aspects are conditioned by the molecular integrity of complex glycosaminoglycans and/or proteoglycans of the perivascular interstitium.

The action that is exerted by the acetylglucosamine and by glucuronic acid with other active ingredients belonging to the class of either monocarboxylic or bicarboxylic α-hydroxy acids also proves to be particularly important in improving the conditions of skin hydration either in the presence of changes of a physiological nature or of a physiopathological or pathological nature.

In case of application for topical use, the keratolytic action exerted by the promotes the absorption of the acetylglucosamine and of the glucuronic acid, making possible a better bioavailability of the two active ingredients and thus a more marked stimulating action on the biosynthesis of the glycosaminoglycans.

The combination of acetylglucosamine and glucuronic acid with hyaluronic acid (in the polymer form) also proves to be particularly positive in the case of subcutaneous or intradermal use.

In fact, the use of hyaluronic acid injected in the dermis, thanks to its property of holding considerable amounts of water, makes it possible to raise the skin, reducing the presence of wrinkles thanks to a physical type action.

Since the hyaluronic acid injected intradermally is degraded in relatively short times, the endogenous, stimulating action of hyaluronic acid performed by acetylglucosamine and by glucuronic acid appears to be justified.

The various features of novelty which characterize the invention are pointed out with particularity in the claims annexed to and forming a part of this disclosure. For a better understanding of the invention, its operating advantages and specific objects attained by its uses, reference is made to the accompanying descriptive matter in which preferred embodiments of the invention are illustrated.

DESCRIPTION OF THE PREFERRED EMBODIMENT

When used alone, the acetylglucosamine may be contained in the composition in an amount of 0.01 to 30 wt. %, and preferably from 0.05 to 15 wt. %, based on the final formulation.

When used alone, the glucuronic acid may be contained in the composition in an amount of 0.001 to 20 wt. %, and preferably from 0.05 to 30 wt. %, based on the final formulation.

When used combined, the acetylglucosamine and the glucuronic acid (or the glucuronolactone) may be contained in the composition in an amount of 0.0001 to 50 wt. % each, and preferably in an amount equal to 0.05 to 15 wt. % each.

In addition, the composition based on acetylglucosamine and/or glucuronic acid may contain various active ingredients, which we will define as synergists for descriptive simplicity.

The synergists may be selected from the group comprising carboxylic acids, α-hydroxy acids and β-hydroxy acids, either monocarboxylic or bicarboxylic.

Glycolic acid, lactic acid, hydroxybutyric acid, mandelic acid, tartaric acid, malic acid, salicylic acid, hydroxybenzoic acid, citric acid, lipoic acid (thioctic acid), either in the oxidized or reduced form, intended both in the dextrorotatory and levorotatory forms, as well as the racemic mixtures and the corresponding salts, esters or amides, may be mentioned as examples.

Two or more of these synergists may be present in the composition, alone or combined, together with the acetylglucosamine and/or the glucuronic acid.

Such synergists may be contained in amounts ranging from 0.001 to 50 wt. %, and preferably from 0.5 to 15 wt. %, based on the final formulation when the proportions of the acetylglucosamine and/or of the glucuronic acid are each 0.05 to 15 wt. %.

In addition, the composition of the present invention may contain either liposoluble or water-soluble vitamins.

Examples are: vitamin B1 (or thiamin), vitamin B2 (riboflavin), vitamin B6 (or pyridoxine, pyridoxal, pyridoxamine), niacin (nicotinic acid, nicotinic amide), pantothenic acid, biotin, folic acid (folic acid, folinic acid), vitamin E (tocopherol), vitamin C (ascorbic acid), beta carotene, retinol (vitamin A), retinal, retinoic acid, para-aminobenzoic acid (4-aminobenzoic acid), vitamin F (linoleic acid), vitamin F (linolenic acid), vitamin F (arachidonic acid), vitamin P (rutin), in both the dextrorotatory and levorotatory forms, as well as the related racemic mixtures, and the corresponding salts or esters in the various weight ratios described below.

When present, these substances may be contained in amounts of 0.001 to 10 wt. %, and preferably of 0.05 to 1 wt. % when the proportions of acetylglucosamine and/or glucuronic acid are each from 0.05 to 15 wt. %.

The composition of the present invention may also contain plants, extracts of plant or parts of plants or their extracts, including roots, leaves, fruits, bark, flowering top, in the form of dry, soft or liquid extracts.

The following may be mentioned as examples of these synergists: *Silybum Marianum, Echinacea Angustifolia, Aesculus Hippocsatanum, Calendula Officinalis, Centella Asiatica, Hamamelis Virginiana Vaccinum Myrtillus, Citrus Aurantium Amara, Citrus Aurantium Dulcis, Citrus Limonium, Equisetum Arvense, Glycirrhiza Glabra, Aloe Vera, Ruta Graveolans, Vitis Vinifera* used alone or combined.

The presence of these synergists may be 0.001 to 30 wt. %, and preferably 0.25 to 20 wt. % when acetylglucosamine and/or glucuronic acid are each contained in amount of 0.05 to 15 wt. %.

The composition of the present invention may also contain, either alone or in combination, chemical substances that may be terpenes, triterpenes, saponins, isoflavonoids, alcohol flavonoids, and the like.

*Anthocyanidins of the bilberry, escin, madecassic acid, madecassosides, asiaticosides, asiatic acid, rutin* and its derivatives, including the salts and esters thereof, *diosmin, sericic acid, sericosides, echinacosides, echinacin, glycerretic acid* and its salts or esters, *quercitin, isoquercitin, bisabolene, silymarin, cyanidins, leucocyanidins,* although contained in plant extracts or plant parts (including leaves, roots, fruits, bark) and the corresponding salts or esters, may be mentioned as examples of these substances.

These substances may be contained in an amount of 0.01 to 20 wt. %, and preferably from 0.05 to 15 wt. %.

The composition of the present invention may contain, alone or combined, substances belonging to the chemical class of amino acids selected from among: alanine arginine, aspartic acid, asparagine, cysteine, glutamic acid, glutamine, glycine, histidine, leucine, isoleucine, lysine, methionine, phenylalanine, proline, serine, threonine, tryptophan, tyrosine, valine, the corresponding salts and esters and the various forms reduced to amino alcohols, both in dextrorotatory and levorotatory form and the related racemic mixtures.

These substances may be contained in amounts of 0.001 to 20 wt. %, and preferably from 0.05 to 15 wt. % when the acetylglucosamine and/or the glucuronic acid are each contained in amounts of 0.05 to 15 wt. %.

The composition of the present invention may contain, alone or combined, substances belonging to the chemical class of the polysaccharides, including hyaluronic acid, chitin, chitosan, dermatan sulfate, and heparin. These substances may be contained in amounts of 0.0001 to 20 wt. %, and preferably from 0.05 to 5 wt. % when the acetylglucosamine and/or the glucuronic acid are each contained in amounts of 0.05 to 15 wt. %.

The combination of acetylglucosamine, of glucuronic acid, or of both with suitable synergists proves to be innovative in the field of cosmetics in dealing with various phenomena associated with the degeneration of aesthetic parameters of the skin. It is particularly useful, but not exclusively, for a moisturizing action, an anti-aging action, anti-wrinkle action, elasticizing action, hardening action, anti-cellulitis action, the cosmetic treatment of baldness, the cosmetic treatment of teleangectasia and of blotchiness.

Its use is also innovative in the pharmaceutical field for the topical treatment of atopic dermatitides, seborrheic dermatitides, nummular eczematous dermatitides, exfoliative dermatitides, stasis dermatitides, neurodermatitides, acne, acne rosacea, cicatricial alopecia, hippocratic alopecia, female-pattern alopecia, drug-induced alopecia, alopecia areata, pseudofolliculitis, psoriasis, lichen ruber planus, ichthyosis, xeroderma, keratosis pilaris, decubitus ulcers, trophic ulcers, torpid sores, vascular spider angiomas, hemangiomas, telangiectatic granuloma, seborrheic keratosis, fibrous histiocytoma, morphea, the treatment of hypertrophic scars, burn scars, teleangectasia, changes in the circulation and the microcirculation, venous stasis, circulatory stasis, lupus erythematosus, topical treatment of scleroderma, and healing of wounds.

The composition of the present invention, which contains acetylglucosamine and/or glucuronic acid optionally with other active ingredients, vitamins, and various additives, may be prepared in formulations for external use, as water-in-oil emulsions, oil-in-water emulsions, monophasic solutions, biphasic pseudo solutions, monophasic gels, biphasic gels or submicellar gels, anhydrous salves, dusting powders, etc., or for internal use, as capsules, tablets, drops, syrups, intramuscular, intravenous, subcutaneous, or intra-articular injections, etc., using the appropriate supports or vehicles.

The composition of the present invention may also be effectively used for internal use in the pharmaceutical field, e.g., in the treatment of degenerative forms of the amorphous component of tissues, circulatory stasis, venous stasis, rheumatoid arthritis, osteoarthritis, arthrosis, scleroderma, etc.

The following preparation examples are further illustrative of and, in the cases specified, descriptive of the composition of the present invention.

In these examples, the proportions, if not indicated otherwise, are in weight percent based on the final composition.

THE USE OF THE COMPOSITION IN THE FORM OF AN EMULSION OBTAINED BY MEANS OF PREPARATION EXAMPLE 1

(Cosmetic and/or Pharmaceutical Use)
Multilamellar-based, Crystalline, Liquid Emulsion Containing Acetylglucosamine, Glucuronic Acid and Diosmin This is a structured oil-in-water emulsion in the form of a multilamellar, crystalline, liquid phase, which is mainly indicated to deal with the problems associated with deficits of a circulatory nature either in the veins or in the microcirculation (capillaries), which can be used either in the pharmaceutical field or in the field of cosmetics (by way of indication, but not exhaustively, for the treatment of liposclerosis, commonly defined cellulitis, heaviness of the legs, teleangectasias of various origins and locations).

The formation of the multilamellar, crystalline liquid phase inside the emulsion is obtained by means of an accurate calibration of a ternary system (x) and by a pentenary system (y), which are represented by three cetyl or stearyl type emulsifying agents and by five chemical entities of a lipid nature, either solid or liquid, also cetyl or stearyl type, respectively.

The particular method of preparation, described below together with types of ingredients used, makes it possible to obtain a mesomorphic phase, in which a multilamellar, crystalline liquid phase with the molecular property of the solid phase and the mobility property of the liquid phase is formed on the surface of the oil micelles.

This particular chemical-physical configuration of the emulsion proves to be visible by means of analysis using polarized-light microscopy.

The structured emulsion in the form of a multilamellar, crystalline liquid phase makes it possible to amplify the action of the product over time, to act as a "reservoir" of active ingredients, proves to be useful in the protection of the active ingredients used, and increases the stability of the emulsion.

Thus, the calibrated combination of acetylglucosamine, of glucuronic acid and diosmin, which are structured in a multilamellar-based, crystalline liquid emulsion, represents an innovation that is able to yield remarkable results.

Water-in-oil Emulsion

|  | Amount in wt. % | |
|---|---|---|
|  | From | to |
| PHASE (A) | | |
| 1. STEARETH-2 | 0.500 | 4.000 (x) |
| 2. CETEARYL GLUCOSIDE | 0.200 | 6.000 (x) |
| 3. PPG-15-STEARYL ETHER | 6.000 | 12.500 (y) |
| 4. STEARETH-21 | 0.100 | 6.400 (x) |
| 5. CETYL ALCOHOL | 0.750 | 6.100 (y) |
| 6. STEARIC ACID | 0.100 | 7.800 (y) |
| 7. CETEARYL ALCOHOL | 0.100 | 5.600 (y) |
| 8. CETEARYL OCTANOATE | 0.200 | 4.000 (y) |
| 9. PHASE (B) | | |
| 10. ACETYLGLUCOSAMINE | 0.100 | 7.900 |
| 11. D-GLUCURONIC ACID GAMMA LACTONE | 0.100 | 7.900 |
| 12. WATER qs. | 5.000 | 5.000 |
| 13. PHASE (C) | | |
| 14. DIOSMIN | 0.100 | 4.750 |
| 15. WATER qs. | 100 | 100 |

Method of Preparation:

1. Heat phase A) to +80° C. and then heat phase C) to +72° C. Combine phase C) with phase A) and homogenize for 15 minutes at 2,500 rpm, under agitation and aspirated vacuum.

2. Initiate a slow cooling with a reduction of 2.5° C. every 4 minutes.

3. At +45° C., homogenize at 3,000 rpm for 7 minutes continually under agitation.

4. At +40° C., add phase B) under agitation and allow to cool to a temperature of 30° C., continually under agitation.

5. Upon reaching 30° C., homogenize for 10 minutes at 2,000 rpm.

PREPARATION EXAMPLE 2
(Cosmetic Use)
Multilamellar-based, Crystalline, Liquid Emulsion Containing Acetylglucosamine, Glucuronic Acid and Silymarin, Tocopherol This is a structured oil-in-water emulsion in the form of a multilamellar, crystalline, liquid phase, which is mainly indicated to deal with the problems associated with the typical problems of skin, which is sensitive and can easily turn red, and with problems of the formation of teleangectasias.

The present formulation has a marked antioxidant effect, which is able to prevent or hinder the phenomena linked with aging of the skin.

The present formulation also proves to be indicated for hindering the symptoms of acne rosacea, mainly but not exclusively in the initial clinical stages.

The formation of the multilamellar, crystalline liquid phase inside the emulsion is obtained by means of an accurate calibration of a ternary system (x) and by a pentenary system (y), which are represented by three cetyl or stearyl type emulsifying agents and by five chemical entities of a lipid nature, either solid or liquid, also cetyl or stearyl type, respectively.

The particular method of preparation, together with types of ingredients used, makes it possible to obtain a mesomorphic phase, in which a multilamellar, crystalline liquid phase with the molecular property of the solid phase and the mobility property of the liquid phase is formed on the surface of the oil micelles.

This particular chemical-physical configuration of the emulsion proves to be visible by means of analysis using polarized-light microscopy.

The structured emulsion in the form of a multilamellar, crystalline liquid phase makes it possible to amplify the action of the product over time, to act as a "reservoir" of active ingredients, proves to be useful in the protection of the active ingredients used, and increases the stability of the emulsion.

Thus, the calibrated combination of acetylglucosamine, of glucuronic acid, of silymarin and of tocopherol, which are structured in a multilamellar-based, crystalline liquid emulsion, represents an innovation that is able to yield remarkable results.

Water-in-oil Emulsion

|  | Amount in wt. % | |
|---|---|---|
|  | From | to |
| PHASE (A) | | |
| 1. STEARETH-2 | 0.500 | 4.000 (x) |
| 2. CETEARYL GLUCOSIDE | 0.200 | 6.000 (x) |
| 3. PPG-15-STEARYL ETHER | 6.000 | 12.500 (y) |
| 4. STEARETH-21 | 0.100 | 6.400 (x) |
| 5. CETYL ALCOHOL | 0.750 | 6.100 (y) |
| 6. STEARIC ACID | 0.100 | 7.800 (y) |
| 7. CETEARYL ALCOHOL | 0.100 | 5.600 (y) |
| 8. CETEARYL OCTANOATE | 0.200 | 4.000 (y) |
| 9. TOCOPHERYL ACETATE | 0.100 | 7.000 |

-continued

|  | Amount in wt. % | |
|---|---|---|
|  | From | to |
| 10. PHASE (B) | | |
| 11. ACETYLGLUCOSAMINE | 0.100 | 7.900 |
| 12. D-GLUCURONIC ACID GAMMA LACTONE | 0.100 | 7.900 |
| 13. WATER qs. | 5.000 | 5.000 |
| 14. PHASE (C) | | |
| 15. SILYMARIN | 0.100 | 4.750 |
| 16. WATER qs. | 100 | 100 |

Method of Preparation:

6. Heat phase A) to +80° C. and then heat phase C) to +72° C. Combine phase C) with phase A) and homogenize for 15 minutes at 2,500 rpm, under agitation and aspirated vacuum.

7. Initiate a slow cooling with a reduction of 2.5° C. every 4 minutes.

8. At +45° C., homogenize at 3,000 rpm for 7 minutes continually under agitation.

9. At +40° C., add phase B) under agitation and allow to cool to a temperature of 30° C., continually under agitation.

10. Upon reaching 30° C., homogenize for 10 minutes at 2,000 rpm.

PREPARATION EXAMPLE 3
(Cosmetic and/or Pharmaceutical Use)
Multilamellar-based, Crystalline, Liquid Emulsion Containing Acetylglucosamine, Glucuronic Acid, Asiatic Acid, Proline This is a structured oil-in-water emulsion in the form of a multilamellar, crystalline, liquid phase, which is mainly indicated to deal with the problems associated with the degeneration of the elastic characteristics of the skin.

The present formulation has an effect that is able to hinder the formation of hypertrophic scars and keloids.

The present formulation also proves to be indicated for improving the healing of skin lesions.

The formation of the multilamellar, crystalline liquid phase inside the emulsion is obtained by means of an accurate calibration of a ternary system (x) and by a pentenary system (y), which are represented by three cetyl or stearyl type emulsifying agents and by five chemical entities of a lipid nature, either solid or liquid, also cetyl or stearyl type, respectively.

The particular method of preparation, together with types of ingredients used, makes it possible to obtain a mesomorphic phase, in which a multilamellar, crystalline liquid phase with the molecular property of the solid phase and the mobility property of the liquid phase is formed on the surface of the oil micelles.

This particular chemical-physical configuration of the emulsion proves to be visible by means of analysis using polarized-light microscopy.

The structured emulsion in the form of a multilamellar, crystalline liquid phase makes it possible to amplify the action of the product over time, to act as a "reservoir" of active ingredients, proves to be useful in the protection of the active ingredients used, and increases the stability of the emulsion.

Thus, the calibrated combination of acetylglucosamine, of glucuronic acid, of proline, and of asiatic acid, which are structured in a multilamellar-based, crystalline liquid emulsion, represents an innovation that is able to yield remarkable results.

Water-in-oil Emulsion

|  | Amount in wt. % | |
|---|---|---|
|  | From | to |
| PHASE (A) | | |
| 1. STEARETH-2 | 0.500 | 4.000 (x) |
| 2. CETEARYL GLUCOSIDE | 0.200 | 6.000 (x) |
| 3. PPG-15-STEARYL ETHER | 6.000 | 12.500 (y) |
| 4. STEARETH-21 | 0.100 | 6.400 (x) |
| 5. CETYL ALCOHOL | 0.750 | 6.100 (y) |
| 6. STEARIC ACID | 0.100 | 7.800 (y) |
| 7. CETEARYL ALCOHOL | 0.100 | 5.600 (y) |
| 8. CETEARYL OCTANOATE | 0.200 | 4.000 (y) |
| 9. PHASE (B) | | |
| 10. ACETYLGLUCOSAMINE | 0.100 | 7.900 |
| 11. D-GLUCURONIC ACID GAMMA LACTONE | 0.100 | 7.900 |
| 12. PROLINE | 0.050 | 6.000 |
| 13. WATER qs. | 5.000 | 5.000 |
| 14. PHASE (C) | | |
| 15. ASIATIC ACID | 0.010 | 4.750 |
| 16. PROPYLENE GLYCOL | 2.000 | 6.000 |
| 17. WATER qs. | 100 | 100 |

Method of Preparation:
11. Heat phase A) to +80° C. and then heat phase C) to +72° C. Combine phase C) with phase A) and homogenize for 15 minutes at 2,500 rpm, under agitation and aspirated vacuum.

12. Initiate a slow cooling with a reduction of 2.5° C. every 4 minutes.

13. At +45° C., homogenize at 3,000 rpm for 7 minutes continually under agitation.

14. At +40° C., add phase B) under agitation and allow to cool to a temperature of 30° C., continually under agitation.

15. Upon reaching 30° C., homogenize for 10 minutes at 2,000 rpm.

PREPARATION EXAMPLE 4
(Cosmetic and/or Pharmaceutical Use)
Multilamellar-based, Crystalline, Liquid Emulsion Containing Acetylglucosamine, Glucuronic Acid, Sericic Acid This is a structured oil-in-water emulsion in the form of a multilamellar, crystalline, liquid phase, which is mainly indicated to deal with the problems associated with the healing process of a wound and/or of a sore.

The present formulation has a marked effect that is able to improve the aesthetic quality of the scar.

The present formulation proves to be indicated for protecting the scar from the damages caused by solar radiation if either chemical or physical sun filters are added to the formulation.

The formation of the multilamellar, crystalline liquid phase inside the emulsion is obtained by means of an accurate calibration of a ternary system (x) and by a pentenary system (y), which are represented by three cetyl or stearyl type emulsifying agents and by five chemical entities of a lipid nature, either solid or liquid, also cetyl or stearyl type, respectively.

The particular method of preparation, together with types of ingredients used, makes it possible to obtain a mesomorphic phase, in which a multilamellar, crystalline liquid phase with the molecular property of the solid phase and the mobility property of the liquid phase is formed on the surface of the oil micelles.

This particular chemical-physical configuration of the emulsion proves to be visible by means of analysis using polarized-light microscopy.

The structured emulsion in the form of a multilamellar, crystalline liquid phase makes it possible to amplify the action of the product over time, to act as a "reservoir" of active ingredients, proves to be useful in the protection of the active ingredients used, and increases the stability of the emulsion.

Thus, the calibrated combination of acetylglucosamine, of glucuronic acid, and of sericic acid, which are structured in a multilamellar-based, crystalline liquid emulsion, represents an innovation that is able to yield remarkable results.

Water-in-oil Emulsion

|  | Amount in wt. % | |
|---|---|---|
|  | From | to |
| PHASE (A) | | |
| 1. | | |
| 2. STEARETH-2 | 0.500 | 4.000 (x) |
| 3. CETEARYL GLUCOSIDE | 0.200 | 6.000 (x) |
| 4. PPG-15-STEARYL ETHER | 6.000 | 12.500 (y) |
| 5. STEARETH-21 | 0.100 | 6.400 (x) |
| 6. CETYL ALCOHOL | 0.750 | 6.100 (y) |
| 7. STEARIC ACID | 0.100 | 7.800 (y) |
| 8. CETEARYL ALCOHOL | 0.100 | 5.600 (y) |
| 9. CETEARYL OCTANOATE | 0.200 | 4.000 (y) |
| 10. TITANIUM DIOXIDE | 10.000 | 35.000 |
| PHASE (B) | | |
| 11. ACETYLGLUCOSAMINE | 0.100 | 7.900 |
| 12. D-GLUCURONIC ACID GAMMA LACTONE | 0.100 | 7.900 |
| 13. WATER qs. | 5.000 | 5.000 |
| PHASE (C) | | |
| 14. SERICIC ACID | 0.010 | 6.750 |
| 15. WATER qs. | 100 | 100 |

Method of Preparation:
1. Heat phase A) to +80° C. and then heat phase C) to +72° C. Combine phase C) with phase A) and homogenize for 15 minutes at 2,500 rpm, under agitation and aspirated vacuum.

2. Initiate a slow cooling with a reduction of 2.5° C. every 4 minutes.

3. At +45° C., homogenize at 3,000 rpm for 7 minutes continually under agitation.

4. At +40° C., add phase B) under agitation and allow to cool to a temperature of 30° C., continually under agitation.

5. Upon reaching 30° C., homogenize for 10 minutes at 2,000 rpm.

PREPARATION EXAMPLE 5
(Cosmetic Use)
Multilamellar-based, Crystalline, Liquid Emulsion Containing Acetylglucosamine, Glucuronic Acid, Retinol, Tocopherol This is a structured oil-in-water emulsion in the form of a multilamellar, crystalline, liquid phase, which is mainly indicated to deal with the problems associated with the aging of the skin.

The present formulation has a marked antioxidant effect that is able to prevent or hinder the formation of wrinkles.

The formation of the multilamellar, crystalline liquid phase inside the emulsion is obtained by means of an accurate calibration of a ternary system (x) and by a pentenary system (y), which are represented by three cetyl or stearyl type emulsifying agents and by five chemical entities of a lipid nature, either solid or liquid, also cetyl or stearyl type, respectively.

The particular method of preparation, together with types of ingredients used, makes it possible to obtain a mesomorphic phase, in which a multilamellar, crystalline liquid phase with the molecular property of the solid phase and the mobility property of the liquid phase is formed on the surface of the oil micelles.

This particular chemical-physical configuration of the emulsion proves to be visible by means of analysis using polarized-light microscopy.

The structured emulsion in the form of a multilamellar, crystalline liquid phase makes it possible to amplify the action of the product over time, to act as a "reservoir" of active ingredients, proves to be useful in the protection of the active ingredients used, and increases the stability of the emulsion.

Thus, the calibrated combination of acetylglucosamine, of glucuronic acid, of retinol and of tocopherol, which are structured in a multilamellar-based, crystalline liquid emulsion, represents an innovation that is able to yield remarkable results.

Water-in-oil Emulsion

|  | Amount in wt. % | |
|---|---|---|
|  | From | to |
| PHASE (A) | | |
| 1. STEARETH-2 | 0.500 | 4.000 (x) |
| 2. CETEARYL GLUCOSIDE | 0.200 | 6.000 (x) |
| 3. PPG-15-STEARYL ETHER | 6.000 | 12.500 (y) |
| 4. STEARETH-21 | 0.100 | 6.400 (x) |
| 5. CETYL ALCOHOL | 0.750 | 6.100 (y) |
| 6. STEARIC ACID | 0.100 | 7.800 (y) |
| 7. CETEARYL ALCOHOL | 0.100 | 5.600 (y) |
| 8. CETEARYL OCTANOATE | 0.200 | 4.000 (y) |
| 9. RETINYL PALMITATE (1,000,000 IU/g) | 0.050 | 4.000 |
| 10. TOCOPHERYL ACETATE | 0.075 | 10.000 |
| PHASE (B) | | |
| 11. ACETYLGLUCOSAMINE | 0.100 | 7.900 |
| 12. D-GLUCURONIC ACID GAMMA LACTONE | 0.100 | 7.900 |
| 13. WATER qs. | 5.000 | 5.000 |
| PHASE (C) | | |
| 14. GLYCEROL | 0.100 | 8.750 |
| 15. WATER qs. | 100 | 100 |

Method of Preparation:

16. Heat phase A) to +80° C. and then heat phase C) to +72° C. Combine phase C) with phase A) and homogenize for 15 minutes at 2,500 rpm, under agitation and aspirated vacuum.

17. Initiate a slow cooling with a reduction of 2.5° C. every 4 minutes.

18. At +45° C., homogenize at 3,000 rpm for 7 minutes continually under agitation.

19. At +40° C., add phase B) under agitation and allow to cool to a temperature of 30° C., continually under agitation.

20. Upon reaching 30° C., homogenize for 10 minutes at 2,000 rpm.

PREPARATION EXAMPLE 5
(Cosmetic Use)
Multilamellar-based, Crystalline, Liquid Emulsion Containing Acetylglucosamine, Glucuronic Acid, Glycolic Acid This is a structured oil-in-water emulsion in the form of a multilamellar, crystalline, liquid phase, which is mainly indicated to deal with the problems associated with the aging of the skin and with dehydration of the skin.

The present formulation has a marked moisturizing effect and, in case of using high doses of glycolic acid, is able to prevent or hinder the formation of wrinkles by means of a marked exfoliating action and chemical peeling.

The action exerted by the glycolic acid also promotes the penetration into the skin both of the acetylglucosamine and of the glucuronic acid, thus making possible a synchronized action that is able to yield appreciable clinical and aesthetic results.

The formation of the multilamellar, crystalline liquid phase inside the emulsion is obtained by means of an accurate calibration of a ternary system (x) and by a pentenary system (y), which are represented by three cetyl or stearyl type emulsifying agents and by five chemical entities of a lipid nature, either solid or liquid, also cetyl or stearyl type, respectively.

The particular method of preparation, together with types of ingredients used, makes it possible to obtain a mesomorphic phase, in which a multilamellar, crystalline liquid phase with the molecular property of the solid phase and the mobility property of the liquid phase is formed on the surface of the oil micelles.

This particular chemical-physical configuration of the emulsion proves to be visible by means of analysis using polarized-light microscopy.

The structured emulsion in the form of a multilamellar, crystalline liquid phase makes it possible to amplify the action of the product over time, to act as a "reservoir" of active ingredients, proves to be useful in the protection of the active ingredients used, and increases the stability of the emulsion.

Thus, the calibrated combination of acetylglucosamine, of glucuronic acid, and of glycolic acid, which are structured in a multilamellar-based, crystalline liquid emulsion, represents an innovation that is able to yield remarkable results.

Water-in-oil Emulsion

|  | Amount in wt. % | |
|---|---|---|
|  | From | to |
| PHASE (A) | | |
| 16. STEARETH-2 | 0.500 | 4.000 (x) |
| 17. CETEARYL GLUCOSIDE | 0.200 | 6.000 (x) |
| 18. PPG-15-STEARYL ETHER | 6.000 | 12.500 (y) |
| 19. STEARETH-21 | 0.100 | 6.400 (x) |
| 20. CETYL ALCOHOL | 0.750 | 6.100 (y) |
| 21. STEARIC ACID | 0.100 | 7.800 (y) |
| 22. CETEARYL ALCOHOL | 0.100 | 5.600 (y) |
| 23. CETEARYL OCTANOATE | 0.200 | 4.000 (y) |
| 24. RETINYL PALMITATE (1,000,000 IU/g) | 0.050 | 4.000 |
| 25. TOCOPHERYL ACETATE | 0.075 | 10.000 |
| PHASE (B) | | |
| 26. ACETYLGLUCOSAMINE | 0.100 | 7.900 |
| 27. D-GLUCURONIC ACID GAMMA LACTONE | 0.100 | 7.900 |
| 28. WATER qs. | 5.000 | 5.000 |
| PHASE (C) | | |
| 29. GLYCEROL | 0.100 | 8.750 |
| 30. WATER qs. | 100 | 100 |

Method of Preparation:

21. Heat phase A) to +80° C. and then heat phase C) to +72° C. Combine phase C) with phase A) and homogenize for 15 minutes at 2,500 rpm, under agitation and aspirated vacuum.

22. Initiate a slow cooling with a reduction of 2.5° C. every 4 minutes.

23. At +45° C., homogenize at 3,000 rpm for 7 minutes continually under agitation.

24. At +40° C., add phase B) under agitation and allow to cool to a temperature of 30° C., continually under agitation.

25. Upon reaching 30° C., homogenize for 10 minutes at 2,000 rpm.

Preparation for Pharmaceutical Use
Pharmaceutical Form: Vial for intradermal injection

|   | From | to |
|---|---|---|
| 1. ACETYLGLUCOSAMINE | 0.0010 | 2.500 |
| 2. GLUCURONIC ACID | 0.0005 | 2.500 |
| 3. HYALURONIC ACID | 0.0500 | 50.00 |
| 4. PHYSIOLOGICAL WATER qs. | 100 | 100 |
| 5. PRESERVATIVE qs. |  |  |

Method of Preparation

Dissolve 1.+2.+5. in 4. Add 3. to the solution obtained. Allow to solvate until a clear gel is obtained. Sterilize and then package in vial.

Preparation for Pharmaceutical Use in Capsules or Tablets
Composition per Unit of Administration

| 1. ACETYLGLUCOSAMINE | 50 mg |
|---|---|
| 2. GLUCURONIC ACID | 50 mg |
| 3. LACTOSE | 70 mg |
| 4. MAGNESIUM STEARATE | 3 mg |

Method of Preparation:

Mix 1+2.+3.+4. after having provided the various ingredients with equal particle size. Then compress or encapsulate.

Preparation for Pharmaceutical or Dietetic Use

| 1. ACETYLGLUCOSAMINE | 15 mg |
|---|---|
| 2. GLUCURONIC ACID | 15 mg |
| 3. LEUCOCYANIDIN | 90 mg |
| 4. TOCOPHEROL | 5 mg |
| 5. SELENIUM | 1 mcg |
| 6. LACTOSE | 50 mg |
| 7. MAGNESIUM STEARATE | 2 mg |

Method of Preparation:

Mix 1.+2.+3.+4.+5.+6.+7. after having provided the various ingredients with equal particle size. Then compress or encapsulate.

While specific embodiments of the invention have been shown and described in detail to illustrate the application of the principles of the invention, it will be understood that the invention may be embodied otherwise without departing from such principles.

What is claimed is:

1. Composition for therapeutic cosmetic, pharmaceutical or dietetic use comprising a pharmaceutical vehicle containing as active ingredient an effective amount of at least one individual compound selected from the group consisting of the individual compound acetylglucosamine and the individual compound glucuronic acid, and at least one substance selected from the group consisting of monocarboxylic acids, dicarboxylic acids, α-hydroxy acids, β-hydroxy acids, plants and extracts thereof, flavonoids, bioflavonoids, isoflavonoids, saponins, terpenes, triterpenes, amino acids, water-soluble vitamins and lipo-soluble vitamins.

2. Composition of claim 1 wherein said substance is at least one acid selected from the group consisting of glycolic acid, lactic acid, hydroxybutyric acid, mandelic acid, tartaric acid, malic acid, hydroxybenzoic acid, citric acid, lipoic acid, and the corresponding salts and esters thereof.

3. Composition of claim 1 wherein said substance is at least one vitamin substance selected from the group consisting of vitamin B1, vitamin B2, vitamin B6, niacin, pantothenic acid, biotin, folic acid, ascorbic acid, beta carotene, retinol, retinal, retinoic acid, p-aminobenzoic acid, tocopherol and vitamin F.

4. Composition of claim 1 wherein said substance is at least one plant or extract thereof selected from the group consisting of *Vaccinum Myrtillus, Sylibum Marianum, Echinacea Angustifolia, Aesculus Hippocastanum, Calendula Officinalis, Centella Asiatica, Hamamelis Virginiana, Citrus Aurantium Amara, Citrus Aurantium Dulcis, Citrus Limonium, Equisetum Arvense, Glycyrritia Glabbra, Aloe Vera, Ruta Graveolans, Vitis Vinifera* and *Terminalia Sericea.*

5. Composition of claim 1 wherein said substance is at least one amino acid selected from the group consisting of alanine, arginine, aspartic acid, asparagine, cysteine, glutamic acid, glutamine, glycine, histidine, leucine, isoleucine, lysine, methionine, phenylalanine, proline, serine, threonine, tryptophan, tyrosine, valine, the corresponding salts and esters thereof, and the corresponding amino alcohols thereof.

6. Composition of claim 1 wherein said substance is at least one substance selected from the group consisting of terpenes, triterpenes, saponins, isoflavonoids, flavonoids and bioflavonoids.

7. Composition of claim 6 wherein said substance is at least one substance selected from the group consisting of anthocyanidins of the bilberry, escin, madecassic acid, madecassosides, asiaticosides, asiatic acid, rutin and its derivatives, diosmin, sericic acid, sericosides, echinacosides, echinacin, glycerretic acid, quercitin, isoquercitin, bisabolene, silymarin, cyanidins, leucocyanidins, and the corresponding salts and esters thereof.

8. Composition for therapeutic cosmetic, pharmaceutical or dietetic use comprising a pharmaceutical vehicle containing as active ingredient an effective amount of at least one individual compound selected from the group consisting of the individual compound acetylglucosamine and the individual compound glucuronic acid, and at least one sulfated or unsulfated polysaccharide selected from the group consisting of hyaluronic acid, chitin, dermatan sulfate, heparin, and the corresponding salts and esters thereof.

9. Composition for therapeutic cosmetic, pharmaceutical or dietetic use comprising a pharmaceutical vehicle containing as active ingredient an effective amount of at least one individual compound selected from the group consisting of the individual compound acetylglucosamine and the individual compound glucuronic acid, and at least one substance selected from the group consisting of diosmin, silymarin, tocopherol, asiatic acid, proline, sericic acid, retinol, glycolic acid, hyaluronic acid and leucocyanidin.

10. Method of therapeutically treating the skin of a subject against the effects of aging or to promote healing of skin injury or infection comprising administering to the skin of the subject an effective amount of a composition comprising as active ingredient at least one individual compound selected from the group consisting of the individual compound acetylglucosamine and the individual compound glucuronic acid.

11. Method of claim 10 wherein the composition further comprises at least one substance selected from the group consisting of monocarboxylic acids, dicarboxylic acids, α-hydroxy acids, β-hydroxy acids, plants and extracts thereof, flavonoids, bioflavonoids, isoflavonoids, saponins, terpenes, triterpenes, amino acids, water-soluble vitamins and lipo-soluble vitamins.

12. Method of claim 10 wherein the composition further comprises at least one acid selected from the group consisting of glycolic acid, lactic acid, hydroxybutyric acid, mandelic acid, tartaric acid, malic acid, hydroxybenzoic acid, citric acid, lipoic acid, and the corresponding salts and esters thereof.

13. Method of claim 10 wherein the composition further comprises at least one vitamin substance selected from the group consisting of vitamin B1, vitamin B2, vitamin B6, niacin, pantothenic acid, biotin, folic acid, ascorbic acid, beta carotene, retinol, retinal, retinoic acid, p-aminobenzoic acid, tocopherol and vitamin F.

14. Method of claim 10 wherein the composition further comprises at least one plant or extract thereof selected from the group consisting of *Vaccinum Myrtillus, Sylibum Marianum, Echinacea Angustifolia, Aesculus Hippocastanum, Calendula Officinalis, Centella Asiatica, Hamamelis Virginiana, Citrus Aurantium Amara, Citrus Aurantium Dulcis, Citrus Limonium, Equisetum Arvense, Glycyrritia Glabbra, Aloe Vera, Ruta Graveolans, Vitis Vinifera* and *Terminalia Sericea*.

15. Method of claim 10 wherein the composition further comprises at least one amino acid selected from the group consisting of alanine, arginine, aspartic acid, asparagine, cysteine, glutamic acid, glutamine, glycine, histidine, leucine, isoleucine, lysine, methionine, phenylalanine, proline, serine, threonine, tryptophan, tyrosine, valine, the corresponding salts and esters thereof, and the corresponding amino alcohols thereof.

16. Method of claim 10 wherein the composition further comprises at least one substance selected from the group consisting of terpenes, triterpenes, saponins, isoflavonoids, flavonoids and bioflavonoids.

17. Method of claim 10 wherein the composition further comprises at least one substance selected from the group consisting of *anthocyanidins of the bilberry, escin, madecassic acid, madecassosides, asiaticosides, asiatic acid, rutin* and its derivatives, *diosmin, sericic acid, sericosides, echinacosides, echinacin, glycerretic acid, quercitin, isoquercitin, bisabolene, silymarin, cyanidins, leucocyanidins,* and the corresponding salts and esters thereof.

18. Method of claim 10 wherein the composition further comprises at least one sulfated or unsulfated polysaccharide selected from the group consisting of hyaluronic acid, chitin, dermatan sulfate, heparin, and the corresponding salts and esters thereof.

19. Method of claim 10 wherein the composition further comprises at least one substance selected from the group consisting of diosmin, silymarin, tocopherol, asiatic acid, proline, sericic acid, retinol, glycolic acid, hyaluronic acid and leucocyanidin.

20. Composition for therapeutic cosmetic, pharmaceutical or dietetic use comprising a pharmaceutical vehicle containing as active ingredient an effective amount of at least one individual compound selected from the group consisting of 0.001–30% by weight of the individual compound acetylglucosamine and the individual compound glucuronic acid.

21. Composition for therapeutic cosmetic, pharmaceutical or dietetic use comprising a pharmaceutical vehicle containing as active ingredient an effective amount of at least one individual compound selected from the group consisting of the individual compound acetylglucosamine and 0.001–30% by weight of the individual compound glucuronic acid.

22. Composition of claim 21 wherein the individual compound acetylglucosamine and the individual compound glucuronic acid are present in equimolar amounts.

23. Composition for therapeutic cosmetic, pharmaceutical or dietetic use comprising a pharmaceutical vehicle containing as active ingredient an effective amount of at least one individual compound selected from the group consisting of 0.05–10% by weight of the individual compound acetylglucosamine and 0.05–10% by weight of the individual compound glucuronic acid.

* * * * *